(12) United States Patent
Kosiorek et al.

(10) Patent No.: US 11,324,516 B2
(45) Date of Patent: May 10, 2022

(54) PNEUMATIC TOURNIQUET APPARATUS AND METHOD OF USE

(71) Applicants: Christopher B. Kosiorek, La Vernia, TX (US); Dexter C. Drayton, San Antonio, TX (US); Esra Abir, New York, NY (US); Neslihan Damar, Istanbul (TR); Nilufer Polat, Brooklyn, NY (US); Yavuz Avci, Sunnyside, NY (US)

(72) Inventors: Christopher B. Kosiorek, La Vernia, TX (US); Dexter C. Drayton, San Antonio, TX (US); Esra Abir, New York, NY (US); Neslihan Damar, Istanbul (TR); Nilufer Polat, Brooklyn, NY (US); Yavuz Avci, Sunnyside, NY (US)

( * ) Notice: Subject to any disclaimer, the term of this patent is extended or adjusted under 35 U.S.C. 154(b) by 235 days.

(21) Appl. No.: 16/369,902

(22) Filed: Mar. 29, 2019

(65) Prior Publication Data
US 2020/0022707 A1 Jan. 23, 2020

Related U.S. Application Data

(62) Division of application No. 14/500,191, filed on Sep. 29, 2014, now Pat. No. 10,271,855.
(Continued)

(51) Int. Cl.
*A61B 17/135* (2006.01)
*A61B 17/00* (2006.01)
(Continued)

(52) U.S. Cl.
CPC ........ *A61B 17/135* (2013.01); *A61B 17/1327* (2013.01); *A61B 90/90* (2016.02);
(Continued)

(58) Field of Classification Search
CPC .............. A61B 17/132; A61B 17/1322; A61B 17/1325; A61B 17/1327; A61B 17/135; A61B 17/1355
See application file for complete search history.

(56) References Cited

U.S. PATENT DOCUMENTS

| | | |
|---|---|---|
| 1,406,770 A | 2/1922 | Smith |
| 2,084,212 A | 6/1937 | Moreira |

(Continued)

FOREIGN PATENT DOCUMENTS

| | | |
|---|---|---|
| AU | 2014324601 B2 | 4/2015 |
| AU | 2014324601 A1 | 5/2016 |

(Continued)

OTHER PUBLICATIONS

"Examiner's report Received for Canada Application 2,929,226, dated Nov. 12, 2020."
(Continued)

*Primary Examiner* — Todd J Scherbel
(74) *Attorney, Agent, or Firm* — Kutak Rock LLP; Brian L. Main

(57) ABSTRACT

A pre-fabricated pneumatic tourniquet apparatus and related methods are provided. The tourniquet is easy to apply, ensures consistent and even circumferential pressure, is light weight, provides standard life saving operation, and can be utilized in any setting or situation. The pneumatic tourniquet apparatus is comprised of a bladder, a reservoir chassis, a retaining cover, a receiver and a slider. The bladder is elongated in shaped—long enough to wrap around most human limbs.

15 Claims, 6 Drawing Sheets

Related U.S. Application Data

(60) Provisional application No. 61/883,797, filed on Sep. 27, 2013.

(51) Int. Cl.
*A61B 17/132* (2006.01)
*A61B 90/90* (2016.01)

(52) U.S. Cl.
CPC ............... *A61B 2017/00526* (2013.01); *A61B 2017/00544* (2013.01); *Y10T 29/49826* (2015.01)

(56) References Cited

U.S. PATENT DOCUMENTS

| | | |
|---|---|---|
| 2,084,412 A | 6/1937 | Schaefer |
| 2,387,428 A | 10/1945 | Brothers |
| 2,410,880 A | 11/1946 | Hennicke |
| 2,528,078 A | 10/1950 | Quilter |
| 2,702,551 A | 2/1955 | Hobson et al. |
| 2,754,825 A | 7/1956 | Richmond |
| 2,841,149 A | 7/1958 | Marsden |
| 2,893,394 A | 7/1959 | Thomsen |
| 3,120,846 A | 2/1964 | Fletcher |
| 3,165,803 A | 1/1965 | Gaylord |
| 3,492,995 A | 2/1970 | Ceravolo |
| 3,910,280 A | 10/1975 | Talonn |
| 4,102,343 A | 7/1978 | Schneider |
| 4,125,115 A | 11/1978 | Mayo et al. |
| 4,149,540 A | 4/1979 | Hasslinger |
| 4,273,130 A | 6/1981 | Simpson |
| 4,279,367 A | 7/1981 | Jacobs |
| 4,501,027 A | 2/1985 | Olsson |
| 4,516,576 A | 5/1985 | Kirchner |
| 4,640,281 A | 2/1987 | Sturm et al. |
| 4,724,829 A | 2/1988 | Knapps |
| 4,911,162 A | 3/1990 | Wolff |
| 5,295,996 A | 3/1994 | Blair |
| 5,304,202 A | 4/1994 | Stahl |
| 5,312,350 A | 5/1994 | Jacobs |
| 5,314,437 A | 5/1994 | Holtsch |
| 5,372,575 A | 12/1994 | Sebastian |
| 5,413,582 A | 5/1995 | Eaton |
| 5,451,234 A | 9/1995 | Wassermann |
| 5,607,448 A | 3/1997 | Stahl et al. |
| 5,649,954 A | 7/1997 | McEwen |
| 5,690,672 A | 11/1997 | Cohen |
| 5,893,870 A | 4/1999 | Talen et al. |
| 6,053,169 A | 4/2000 | Hunt |
| 6,131,972 A | 10/2000 | Whitehead et al. |
| 6,682,547 B2 | 1/2004 | McEwen et al. |
| 6,746,470 B2 | 6/2004 | McEwen et al. |
| 6,833,001 B1 | 12/2004 | Chao |
| 6,884,254 B2 | 4/2005 | Brooks |
| 6,899,720 B1 | 5/2005 | McMillan |
| 6,960,023 B2 | 11/2005 | Hsu et al. |
| 6,960,223 B1 | 11/2005 | Ambach |
| 7,468,067 B2 | 12/2008 | Licata et al. |
| 7,582,102 B2 | 9/2009 | Heinz et al. |
| 7,604,651 B1 | 10/2009 | Harris et al. |
| 7,776,064 B2 | 8/2010 | Jennifer et al. |
| 7,842,067 B2 | 11/2010 | Esposito |
| 7,892,253 B2 | 2/2011 | Esposito et al. |
| D649,642 S | 11/2011 | Johnson |
| 8,047,850 B2 | 11/2011 | Esposito et al. |
| 8,303,620 B2 | 11/2012 | Johnson et al. |
| 8,343,182 B2 | 1/2013 | Kirkham |
| 8,348,970 B2 | 1/2013 | Janota |
| 8,425,551 B2 | 4/2013 | McEwen et al. |
| 8,486,106 B2 | 7/2013 | Warburton |
| 8,568,341 B2 | 10/2013 | Flood |
| 8,707,468 B2 | 4/2014 | Reynolds et al. |
| 8,834,517 B2 | 9/2014 | Croushorn et al. |
| 8,863,333 B2 | 10/2014 | Cain et al. |
| 8,926,651 B2 | 1/2015 | McDonald et al. |
| 9,855,055 B2 | 1/2018 | Kosiorek et al. |
| 10,271,855 B2* | 4/2019 | Kosiorek ............ A61B 17/135 |
| 10,278,708 B2 | 5/2019 | Demas et al. |
| 10,716,577 B2 | 7/2020 | Kosiorek et al. |
| 2003/0028215 A1 | 2/2003 | Brooks |
| 2003/0139766 A1 | 7/2003 | McEwen et al. |
| 2004/0226150 A1 | 11/2004 | Beletsky |
| 2005/0240217 A1 | 10/2005 | Jennifer et al. |
| 2005/0267518 A1 | 12/2005 | Wright et al. |
| 2005/0273134 A1 | 12/2005 | Esposito |
| 2006/0095072 A1 | 5/2006 | Tenbrink et al. |
| 2006/0281611 A1* | 12/2006 | Sato ................. A63B 21/4025 482/148 |
| 2007/0038243 A1 | 2/2007 | Rutherford |
| 2007/0185428 A1 | 8/2007 | Harder |
| 2007/0250109 A1 | 10/2007 | Kerstein et al. |
| 2008/0183207 A1 | 7/2008 | Horne |
| 2008/0209650 A1 | 9/2008 | Brewer et al. |
| 2008/0262534 A1 | 10/2008 | O'Neil |
| 2008/0281351 A1 | 11/2008 | Croushorn et al. |
| 2008/0312682 A1 | 12/2008 | Shams et al. |
| 2009/0024159 A1 | 1/2009 | Nee et al. |
| 2009/0062842 A1 | 3/2009 | Esposito et al. |
| 2010/0049241 A1 | 2/2010 | Persson |
| 2010/0057120 A1 | 3/2010 | Kirkham |
| 2011/0178546 A1 | 7/2011 | Johnson et al. |
| 2011/0204114 A1 | 8/2011 | Miller |
| 2011/0214259 A1 | 9/2011 | Kosh et al. |
| 2011/0307004 A1 | 12/2011 | Johnson et al. |
| 2011/0313435 A1 | 12/2011 | Aldridge et al. |
| 2012/0071917 A1 | 3/2012 | McDonald et al. |
| 2012/0260463 A1 | 10/2012 | Hines |
| 2013/0012857 A1 | 1/2013 | Flynn et al. |
| 2013/0110019 A1 | 5/2013 | Hopman et al. |
| 2013/0110027 A1 | 5/2013 | Kobler |
| 2013/0145554 A1 | 6/2013 | Cane et al. |
| 2013/0296921 A1 | 11/2013 | Saunders et al. |
| 2013/0310872 A1 | 11/2013 | Croushorn et al. |
| 2014/0277103 A1 | 9/2014 | Esposito |
| 2015/0094756 A1 | 4/2015 | Kosiorek et al. |
| 2015/0133991 A1 | 5/2015 | Kosiorek et al. |
| 2016/0302799 A1 | 10/2016 | Esposito |
| 2018/0193033 A1 | 7/2018 | Kosiorek et al. |
| 2020/0229826 A1 | 7/2020 | Kosiorek et al. |

FOREIGN PATENT DOCUMENTS

| | | |
|---|---|---|
| AU | 2014324593 B2 | 5/2018 |
| AU | 2018217338 A1 | 9/2018 |
| AU | 2014324593 C1 | 1/2019 |
| CA | 2929226 A1 | 4/2015 |
| CN | 201469344 U | 5/2010 |
| CN | 203169261 U | 9/2013 |
| DE | 2524968 A1 | 12/1976 |
| DE | 3047723 A1 | 7/1982 |
| DE | 3133793 A1 | 3/1983 |
| DE | 3232418 A1 | 3/1984 |
| EP | 0554602 A1 | 8/1993 |
| EP | 3048998 A1 | 4/2015 |
| EP | 3048997 A1 | 8/2016 |
| GB | 21801 A | 12/1907 |
| GB | 02140 A | 1/1912 |
| GB | 105170 A | 4/1917 |
| GB | 291600 A | 6/1928 |
| GB | 1206605 A | 9/1970 |
| GB | 2126649 A | 3/1984 |
| GB | 8324344 | 3/1984 |
| IN | 1702KOL2007 A | 6/2009 |
| WO | 9205741 A1 | 4/1992 |
| WO | 2005091718 A2 | 10/2005 |
| WO | 2011001431 A1 | 1/2011 |
| WO | 2011072126 A2 | 6/2011 |
| WO | 2012106683 A2 | 8/2012 |
| WO | 2015048660 A1 | 4/2015 |
| WO | 2015048668 A1 | 4/2015 |

(56) References Cited

OTHER PUBLICATIONS

Non-Final Office Action Received for U.S. Appl. No. 15/847,033, dated Aug. 23, 2019, 52 pages.
Notice of Decision to Grant Received for Australian Patent Application No. 2014324601, dated Aug. 15, 2019, 1 Page.
Abdominal Aortic Tourniquet, http://vvww.militarytimes.com/article/20130928/NEWS/309280006/Abdominal-tourniquet-gives-lifesaving-time, accessed Oct. 28, 2014.
Combat Application Tourniquet, http://combattourniquet.com/about/, accessed Oct. 27, 2014.
Communication Pursuant to Rules 161(2) and 162 EPC received for European Application No. 14847757.3, dated Feb. 2, 2017, 2 Pages.
Communication pursuant to Rules 70(2) and 70a(2) EPC received for EP Application No. 14847757.3 dated Jun. 12, 2018.
Extended European Search Report mailed for Application No. 14847757.3 dated May 25, 2018, 9 pages.
Extended European Search Report received for Application No. 14849448.7 dated Jun. 19, 2017, 9 pages.
Final Office Action Received for U.S. Appl. No. 14/500,084, dated Mar. 31, 2017, 18 pages.
Final Rejection Received for U.S. Appl. No. 14/500,191 dated Sep. 12, 2017, 16 pages.
First Examination Report Received for Australian Application No. 2014324601, dated Jun. 15, 2018, 4 pages.
International Preliminary Report on Patentability and Written Opinion received for PCT Application No. PCT/US2014/058079, dated Mar. 29, 2016, 11 Pages.
International Preliminary Report on Patentability and Written Opinion received for PCT Application No. PCT/US2014/058098, dated Mar. 29, 2016, 9 pages.
International Search Report and Written Opinion received for PCT Application No. PCT/US2014/058079, dated Jan. 22, 2015, 12 pages.
International Search Report and Written Opinion Received for PCT Application No. PCT/US2014/058098, dated Jan. 12, 2015, 10 pages.
Kragh Jr. et al., "The Military Emergency Tourniquet Programs Lessons Learned With Devices and Designs," Military Medicine, 2011, vol. 176, No. 10. pp. 1144-1152.
Non-Final Office Action received for U.S. Appl. No. 14/500,084, dated Sep. 2, 2016, 18 pages.
Non-Final Rejection Received for U.S. Appl. No. 14/500,191 dated Mar. 30, 2017, 21 pages.
Notice Of Acceptance Received for Australian Application No. 2014324601, dated Apr. 15, 2019, 3 pages.
Notice of Allowance Received for U.S. Appl. No. 14/500,191, dated Dec. 31, 2018, 21 pages.
Notice of Allowance Received for U.S. Appl. No. 14/500,191, dated Sep. 25, 2018, 10 pages.
Notice of Allowance received for U.S. Appl. No. 14/500,084 dated Aug. 16, 2017, 2 pages.
Notice of Allowance Received for U.S. Appl. No. 14/500,084 dated Aug. 24, 2017, 7 pages.
SAM Junctional Tourniquet, http:1/sammedical.com/wp-content/uploads/2013/09/SJT-206-BR0-4 web.pdf, accessed Oct. 28, 2014.
SOF Tactical Tourniquet Wide, http://www. tacmedsolutions.com/product/sof-tactical-tourniquet -wide/, accessed Oct. 27, 2014.
Walters, T.J. , et al., "Laboratory Evaluation of Battlefield Tourniquets in Human Volunteers," USAISR Technical Report 2005-5, Sep. 30, 2005, 34 pages.
"Examiner's report Received for Canada Application 2,929,226, dated Aug. 13, 2021."
First Examination Report Received for AU Application No. 2018217338, dated Aug. 29, 2019, 6 pages.
Notice of Allowance Received for U.S. Appl. No. 15/847,033 dated Mar. 5, 2020, 10 pages.
Notice of Allowance received for U.S. Appl. No. 14/500,084 dated Aug. 24, 2017, 12 pages.
Notice of Allowance Received for U.S. Appl. No. 14/500,084 dated Jul. 31, 2017, 19 pages.
"Communication Pursuant to Article 94(3) EPC received for Application No. 14849448.7 dated Dec. 8, 2021, 4 pages".

\* cited by examiner

PNEUMATIC TOURNIQUET APPARATUS AND METHOD OF USE

CROSS-REFERENCE TO RELATED APPLICATIONS

This application is a divisional application of co-pending U.S. patent application Ser. No. 14/500,191, filed Sep. 29, 2014, which claims priority pursuant to 35 U.S.C. 119(e) to U.S. Provisional Patent Application Ser. No. 61/883,797, filed Sep. 27, 2013, the entire disclosure of which is incorporated herein by reference.

GOVERNMENT RIGHTS

This invention was made with government support under W81XWH-12-P-0497 awarded by USA MED RESEARCH ACQ ACTIVITY. The government has certain rights in the invention.

FIELD

Embodiments of the present invention are directed to a pneumatic tourniquet and novel blood flow restriction device. In more detail, embodiments of the present invention are directed to an emergency use, pre-fabricated tourniquet used for restricting flow of blood during extreme hemorrhage or exsanguination.

BACKGROUND

Exsanguination or major blood loss has been shown to be the major leading cause of death on the battlefield and directly correlates to major trauma in the civilian sector. Throughout history, tourniquets have been shown to save lives. Several large studies have confirmed the lifesaving benefit and low incidence of complications from pre-hospital use of tourniquets in combat casualties. Furthermore, the civilian Emergency Medical Services have adopted this opinion as well. Tourniquets are frequently used early in the care of trauma casualties because of the immediate lifesaving intervention capability and the speed with which they can be applied. Moreover, tourniquets are the standard of care for the temporary control of life-threatening extremity hemorrhage during the Care Under Fire (CUF) phase of the Tactical Combat Casualty Care (TCCC) in accordance with the Committee for Tactical Combat Casualty Care (CoTCCC) guidelines. These guidelines are becoming the standard of care for treatment of massive hemorrhage across the spectrum of pre-hospital care worldwide.

Due to the nature of traumatic amputation and dismemberment, there is a requirement for application of an emergency tourniquet to be operated by one hand. For a device to be truly operable by only one hand, it must be capable of being placed on an extremity, upper or lower, without having to perform fine motor skill functions. In general, tourniquet operation should not require the use of fine motor skills, regardless of the one-handed operability requirement, because tourniquets are generally only used during periods of extreme duress (i.e., when it is difficult or impossible to expect the use of fine motor skills).

Traditionally, tourniquets were nothing more than a general section of cloth material, usually a cravat, and a stick or dowel used as a windless. The general concept was to tighten the cloth material, reducing the circumference (diameter) of the cloth material against the extremity soft tissue, creating circumferential pressure sufficient enough to occlude blood flow. These make-shift tourniquets were often applied with too much pressure and caused neurovascular damage in limbs. Although the patient's life and limb were saved, the affected limb was permanently damaged. Therefore, a pre-fabricated tourniquet designed for consistent, even circumferential pressure is ideal for emergency use.

Additionally, current tourniquet designs are prone to failure and are generally ineffective for use on lower extremities. Pneumatic tourniquet designs can be more desirable than a windless, mechanical design because pneumatic tourniquets can be more effective at restricting blood flow and can be more comfortable during use. However, because of design and cost constraints, current pneumatic tourniquets are generally only used in Hospital environments and are not effective or mechanically operable for field use.

Furthermore, there are many situations in which a tourniquet can save a life other than in military applications. Some recreational activities can be inherently dangerous and can cause severe injury requiring the use of such an emergency device, especially in a remote setting. Primary examples of this are camping, rock climbing, hiking, boating, etc. Footprint size and weight are always a consideration in such settings since the individual user is required to carry the device in a backpack. Therefore, a ruggedized pre-fabricated tourniquet made of the strong and light material would be best-suited for the end-user. Such a tourniquet would provide for efficient transportation and effective, life-saving utilization.

Thus, there is a need for a pre-fabricated tourniquet that is easy to apply, that ensures consistent and even circumferential pressure, that is light weight, that provides standard life saving operation, and that can be utilized in any setting or situation.

SUMMARY

One object of the general inventive concept is to provide a pneumatically constricting tourniquet apparatus. The pneumatic tourniquet apparatus is made up of a bladder, a reservoir chassis, a retaining cover, a receiver and a slider. The bladder is elongated in shaped—long enough to wrap around most human limbs. In some embodiments, the bladder is formed from a single sheet of plastic, folded over along one edge and sealed along the other three edges so that the bladder holds and maintains air pressure while being inflated.

The reservoir chassis holds and protects the bladder. The reservoir chassis includes a main section that envelops the bladder and a reservoir chassis extension section that extends from the main section but does not envelop the bladder. A retaining cover attached to the reservoir chassis where the main section and the chassis extension section connect. The retaining cover covers and protects the reservoir chassis.

A receiver is connected to either the reservoir chassis or the retaining cover, at a location very near to where the retaining cover is attached to the reservoir chassis. A slider is connected to the retaining cover such that the slider can be slid to any point along the retaining cover. The receiver and slider are sized and shaped such that the slider is temporarily locked in position on the retaining cover as a friction buckle when engaged with the receiver.

Another object of the general inventive concept is to provide a pneumatically constricting tourniquet apparatus. The pneumatic tourniquet apparatus is made up of a bladder placed into a reservoir chassis, a retaining cover attached to the reservoir chassis, a receiver attached to the retaining cover or the reservoir chassis, and a slider attached to the retaining cover. The reservoir chassis includes a main section that holds the bladder and an extension section connected to the main section. The retaining cover is attached to the reservoir chassis at a position adjacent to where the main section of the reservoir chassis connects to the extension section. The receiver is attached to either the retaining cover or the reservoir chassis adjacent to the position where the retaining cover is attached to the reservoir chassis. The slider is attached to the retaining cover such that the slider can slide to numerous positions along the retaining cover. The slider is sized and shaped to engage with the receiver.

Another object of the general inventive concept is to provide a method of making a pneumatically constricting tourniquet apparatus. The method includes sealing a bladder, inserting the bladder into a reservoir chassis, attaching a retaining cover to the reservoir chassis, connecting a receiver to either the reservoir chassis or the retaining cover, and connecting a slider to the retaining cover. In some embodiments, the bladder is formed from a single sheet of plastic, folded over along one edge and sealed along the other three edges so that the bladder holds and maintains air pressure while being inflated. The bladder is inserted into the reservoir chassis to hold and to protect the bladder. The reservoir chassis includes a main section that envelops the bladder and a reservoir chassis extension section that extends from the main section but does not envelop the bladder. The retaining cover is attached to the reservoir chassis where the main section and the chassis extension section connect. The retaining cover covers and protects the reservoir chassis.

A receiver is connected to either the reservoir chassis or the retaining cover at a location near where the retaining cover is attached to the reservoir chassis. The slider is connected to the retaining cover such that the slider can be slid to any point along the retaining cover. The receiver and slider are sized and shaped such that the slider is temporarily locked in position on the retaining cover as a friction buckle when engaged with the receiver.

Another object of the general inventive concept is to provide a method of making a pneumatically constricting tourniquet apparatus. The method includes placing a bladder into a reservoir chassis, attaching a retaining cover to the reservoir chassis, attaching a receiver to the retaining cover or the reservoir chassis, and attaching a slider to the retaining cover. The reservoir chassis includes a main section that holds the bladder and an extension section connected to the main section. The retaining cover is attached to the reservoir chassis at a position adjacent to where the main section of the reservoir chassis connects to the extension section. The receiver is attached to either the retaining cover or the reservoir chassis adjacent to the position where the retaining cover is attached to the reservoir chassis. The slider is attached to the retaining cover such that it can be slid along the retaining cover. The slider is sized and shaped to engage with the receiver.

The foregoing and other objects are intended to be illustrative of the invention and are not meant in a limiting sense. Many possible embodiments of the invention may be made and will be readily evident upon a study of the following specification and accompanying drawings comprising a part thereof. For example, dimensional values included herein are provided for exemplary purposes, and embodiments of the present invention contemplate tourniquets or tourniquet components having a various dimensional values. Furthermore, various features and subcombinations of invention may be employed without reference to other features and subcombinations. Other objects and advantages of this invention will become apparent from the following description taken in connection with the accompanying drawings, wherein is set forth by way of illustration and example, an embodiment of this invention.

DRAWINGS

Embodiments of the invention are set forth herein and are shown in the following drawings.

DETAILED DESCRIPTION

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 1:
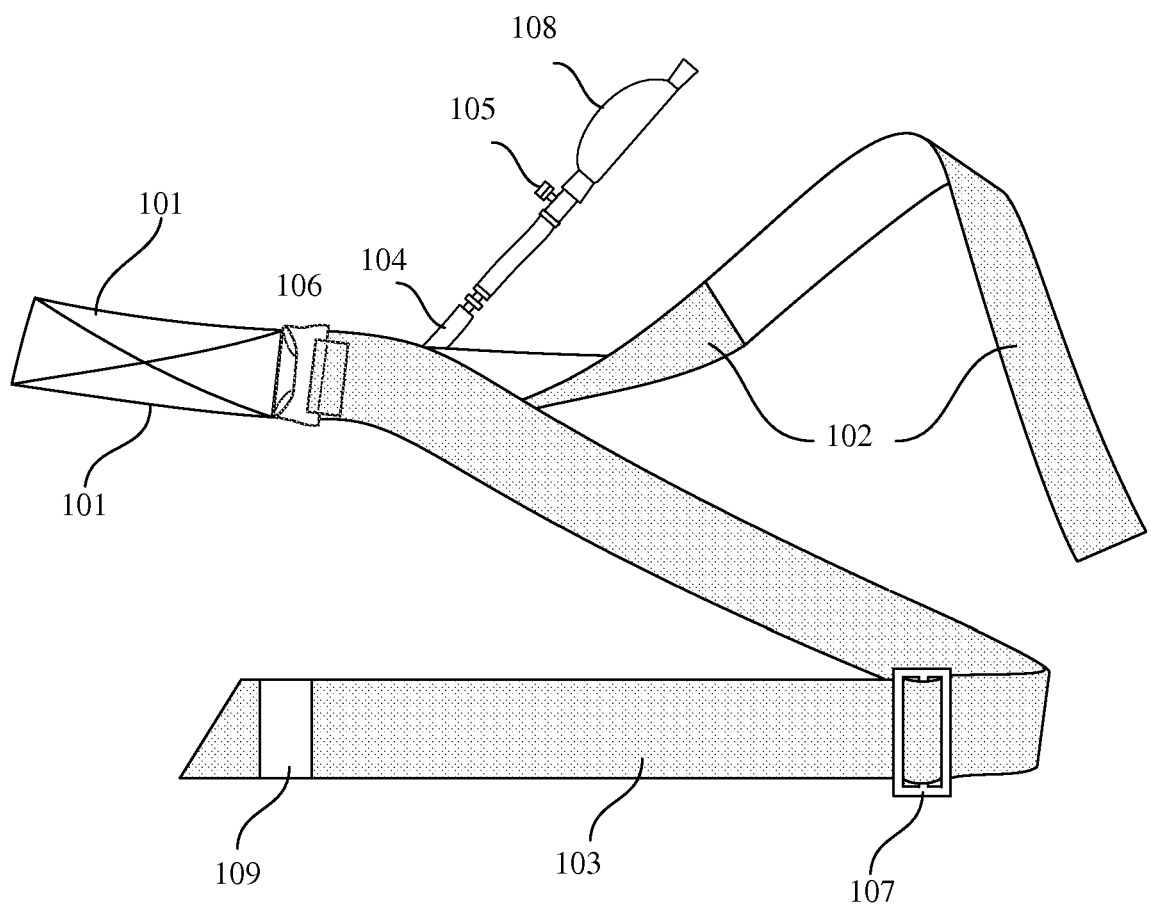
FIG. 1 shows an exemplary pneumatic tourniquet according to embodiments of the present invention.
Figure 2:
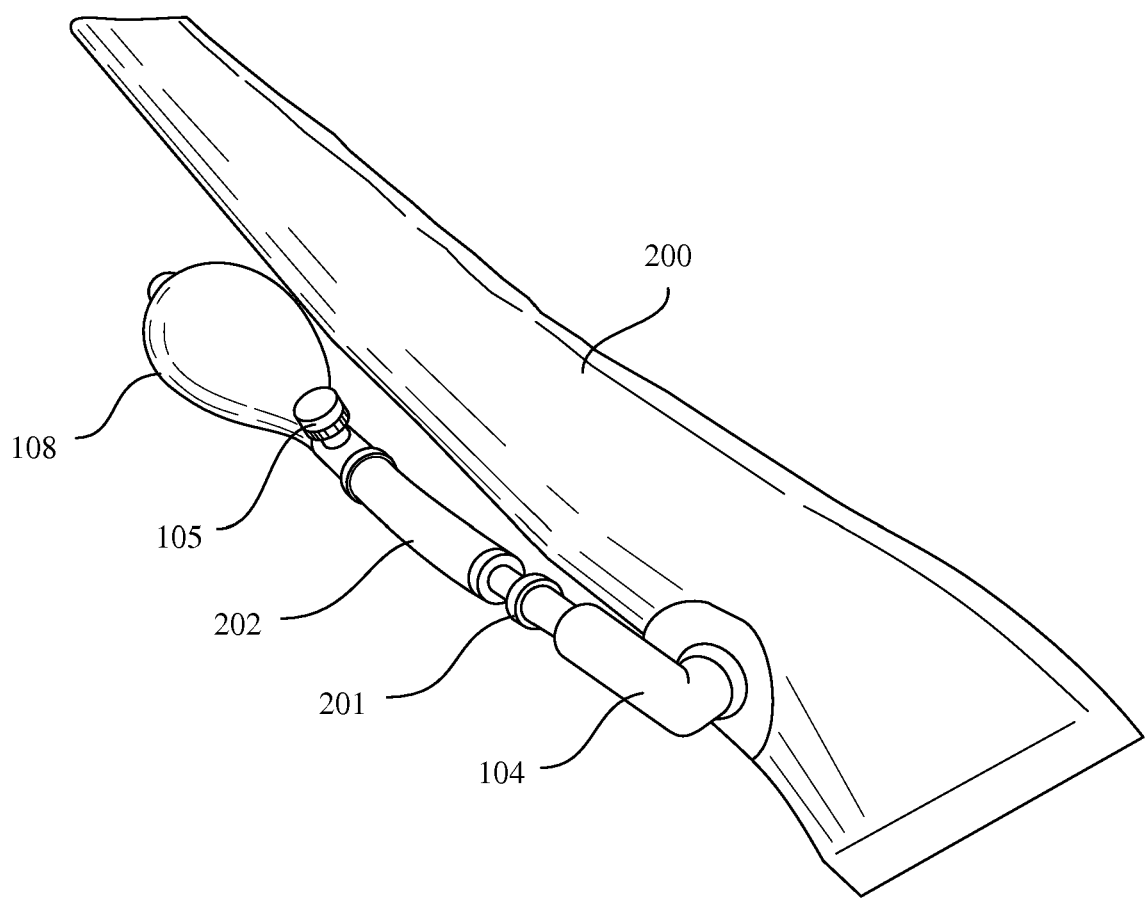
FIG. 2 shows an exemplary bladder that can be positioned within a reservoir chassis of the tourniquet from FIG. 1.
Figure 8:
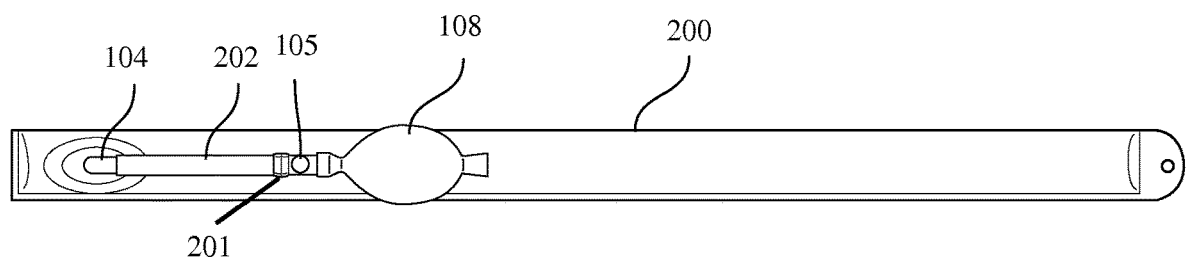
FIG. 8 shows another exemplary bladder that can be positioned within a reservoir chassis of the tourniquet from FIG. 1.

With reference to the figures, and in particular FIG. 1, embodiments of the present invention are directed to a pneumatic tourniquet for restricting a blood flow in a body part, such as an upper or a lower extremity, with the tourniquet comprising: (a) a bladder 200 (See FIGS. 2 and 8) sealed from 3 edges to hold and maintain air pressure while being inflated with an inflation pump 108; (b) a reservoir chassis 102 to hold and to protect the bladder 200, with the reservoir chassis 102 including a main section that holds the bladder 200 and a reservoir chassis extension section 101 that extends from the main section but does not hold the bladder 200; (c) a retaining cover 103 that is attached to the reservoir chassis 102 where the main section and the chassis extension section connect, with the retaining cover 103 operable to cover and protect the reservoir chassis 102 (d) a receiver 106 (See also FIG. 3) connected to either the reservoir chassis 102 or the retaining cover 103 proximate to where the retaining cover 103 is attached to the reservoir chassis 102, with the receiver 106 being operable to accept a slider 107 (See also FIG. 4) that is positioned on the retaining cover 103 from any position along the retaining cover 103, and furthermore with the receiver 106 being operable to allow a user to "snap" the slider 107 into place and lift the lip 303 of the receiver 106 to remove the slider 107 upon demand; (e) the slider 107 serves as a friction buckle operable to be placed along any section of the retaining cover 103, with the slider 107 including one round side bar 401 and one square side bar 402 with grippers 405 allowing for free rotation when attached to the receiver 106. In operation, the pneumatic tourniquet (See also FIGS. 5A-7) is operable, via the above described components (a-e), to form a continuous loop around an extremity, such as an arm or a leg, so as to create a circumferential pressure that will restrict blood flow. Such a circumferential pressure is created by and 1) joining the slider 107 and the receiver 106 together and manipulating the retaining cover 103 so as to reduce the circumference of the tourniquet, and 2) pumping air into the bladder 200.

With respect to FIG. 1 (see also FIGS. 5A-7), the reservoir chassis 102 retains and protects the air bladder 200. In some embodiments, the total length is 33 inches and the width is between 2 and 4 inches. In some embodiments, the reservoir chassis 102 includes a section of dual hook and loop fasteners on both sides of the reservoir chassis faces. In other words, the dual hook and loop fasteners are on the side facing "in" and the side facing "out." The tourniquet also includes a retaining cover 103 sized and shaped to overlap the reservoir chassis 102 as a secondary securing mechanism to prevent slippage or pressure reduction. The retaining cover 103 also provides extra protection for the reservoir chassis 102 and bladder 200. The outer surface of the retaining cover 103 includes dual hook and loop fasteners. The reservoir chassis extension 101 does not contain the bladder 200. The reservoir chassis extension 101 is sized and shaped to accommodate larger arm or leg circumferences. In some embodiments, the reservoir chassis 102 and/or the retaining cover 103 further include a blank label 109. The blank label 109 may be used to write the time when the tourniquet is applied or various other relevant notes regarding patient care.

Extending from the bladder 200 (see also FIGS. 2 and 8) is a nipple 104 that connects the bladder to an air pump. In some embodiments, a half bulb inflation pump 108 is used to pump air into the bladder 200 via the nipple 104. In some embodiments, the half bulb inflation pump 108 is latex free and ergonomically designed for ease of use. In some embodiments, the inflation mechanism includes a relief valve 105 to manually control the release of pressure inside the bladder 200. In some embodiments, the inflation includes a metal clamp 201, such as a small brass ring, attached to the connection between the nipple 104 and the relief valve 105 or inflation pump 108.

In more detail, the retaining cover 103 (See FIGS. 1 and 5A-7) includes dual hook and loop (i.e., Velcro) on its exterior surface and a nylon denier on its interior surface (i.e., the surface that faces the bladder 200). Thus, the retaining cover 103 is operable to cover and protect the reservoir chassis 102 and also operable to secure the tourniquet around an extremity. For example, the retaining cover 103 can be positioned in a continuous loop around an extremity by wrapping the retaining cover 103 around the extremity. Next, the slider 107, which is adjustably secured to the retaining cover 103, can be secured to the receiver 106, which is fixably connected to either the reservoir chassis 102 or the retaining cover 103, as previously described. In such an arrangement, the diameter of the continuous loop can be shortened by pulling the retaining strap further through slider 107, thus creating an increased circumferential pressure (i.e., a radial compression). Once a preferred diameter has been obtained, such a diameter can be maintained by folding the retaining cover 103 back upon itself and securing such a position via the hook and loop of the retaining cover 103.

In some embodiments, the bladder 200 (See FIGS. 2 and 8) of the pneumatic tourniquet is formed from a polyurethane plastic material by sealing 3 edges of the plastic material. Furthermore a nipple 104 is attached to the polyurethane plastic and extends therefrom at an approximately 90 degree angle. From the nipple 104, a silicon tube 202 extends a distance and connects with the pump 108, which may, in some embodiments include a semicircle pressure inflation bulb (e.g., an ergonomically designed hemicycle pressure pump). Embodiments in which the pump 108 is a semicircular face may be preferable in instances when the tourniquet is required to be packaged in a small space. In certain embodiments, the bladder 200 is preferred to hold at least 450 mmHg of pressure, so as to be sufficient to stop blood flow and hemorrhage in an extremity. In other embodiments, the bladder 200 will hold more or less than 450 mmHg. In some embodiments, the bladder 200 will be approximately 25 inches in length, so as to be sufficient for use with human extremities (i.e., arms and legs) that have sizes within the 5th to 95th percentile. Regardless, embodiments of the present invention contemplate bladder lengths that are more or less than 25 inches. Furthermore, in some embodiments, the width of the bladder will be approximately 1.5 inches, which proves for a broad pressure base that can be applied to an extremity. However, it is understood that widths more or less than 1.5 inches may be used in some embodiments. The bladder 200 will, in some embodiments, also include a relief valve 105 that provides for a manual or automatic release of air pressure within the bladder 200.

Embodiments of the present invention provide for the reservoir chassis 102 (See FIGS. 1 and 5A-7) to protect the bladder 200 (See also FIGS. 2 and 8) from environmental damages that may occur during transportation or use of the tourniquet. In some embodiments, the reservoir chassis 102 will be formed in a coyote brown color to uniquely identify a first application of the tourniquet over the circumference of the damaged extremity. In some embodiments, a length of the reservoir chassis 102 is approximately 33 inches. However, in other embodiments, the chassis 102 may be more or less than 33 inches. With the total length of the reservoir chassis 102 being 33 inches, some embodiments provide for the main section to be about 25 inches length (or at least long enough to hold the bladder 200), and the extension section 101 to be about 8 inches in length. In some embodiments, the extension section 101 is included so as to provide for the comfortable placement of the tourniquet onto larger sized extremities. Further, some embodiments provide for two sections of approximately 16 inches of hook and loop to be positioned on an interior and exterior surface of the reservoir chassis. In particular, a first section of hook and loop is positioned on the exterior surface of the reservoir chassis 102 adjacent to an end of the reservoir chassis 102 that is opposite the extension section 101. In some embodiments, more or less than 16 inches of hook and loop will be added to the reservoir chassis 102. In certain additional embodiments, the interior surface of the reservoir chassis 102 will have a section of hook and loop thereon, with the section covering the extension section 101 and extending from the extension section 101 along a portion of the main section. In such embodiments, the main section of the reservoir chassis 102 can be wrapped around an extremity and can be secured in place by connecting the dual hook and loop on the outer surface of the main section with the dual hook and loop on the interior surface of the extension section 101. As such, the tourniquet can be initially positioned over and secured to an extremity until the slider 107 can be connected to the receiver 106 and the retaining cover 103 tightened and secured in a preferred position. Once the retaining cover 103 is tightened and secured in a preferred position, the bladder 200 can be pumped up and filled with air to create the intended circumferential pressure to stop hemorrhaging and blood loss.

In some embodiments, the pneumatic tourniquet includes the retaining cover 103 (See FIGS. 1 and 5A-7) which is sewn with nylon coated fabric and dual hook and loop, as previously described. In some embodiments, the retaining cover 103 is approximately 39 inches length. In other embodiments, the retaining cover 103 may be more or less than 39 inches. The retaining cover 103 preferably overlaps the reservoir chassis 102 as a secondary securing mechanism to prevent any slippage and provides extra protection. The retaining cover 103 includes a time label 109 which is comprised of a clothing label and is inserted on an end of the cover to write the time when application of the tourniquet is made.

Additional embodiments of the present invention include a tourniquet (See FIGS. 1 and 5A-7) that is operable for restricting a flow of blood in a body part, such an upper or a lower extremity, with such a tourniquet comprising: (a) a bladder 200 (See FIGS. 2 and 8) placed into a reservoir chassis 102, with the reservoir chassis 102 including a main section that holds the bladder 200 and an extension section 101 connected to said main section; (b) a retaining cover 103 attached to the reservoir chassis 102 at a position adjacent to where the main section of the reservoir chassis 102 connects to the extension section 101; (c) a receiver 106 (See also FIG. 3) joined with the retaining cover 103 or the reservoir chassis 102 adjacent to the position where the retaining cover 103 is attached to the reservoir chassis 102; and (c) a slider 107 (See also FIG. 4) attached to the retaining cover 103 for quick application to the receiver 106. In such embodiments, when the tourniquet is placed onto the damaged circumference of the extremity, the slider 107 can be attached to the receiver 106 and then the retaining cover 103 can be adjusted to a preferred position so as to create a circumferential pressure. Furthermore, the retaining cover 103 can be secured in such a position by folding an end of the retaining cover 103 back on itself such that the dual hook and loop of the retaining cover 103 secures the retaining cover 103 in place.

Figure 3:
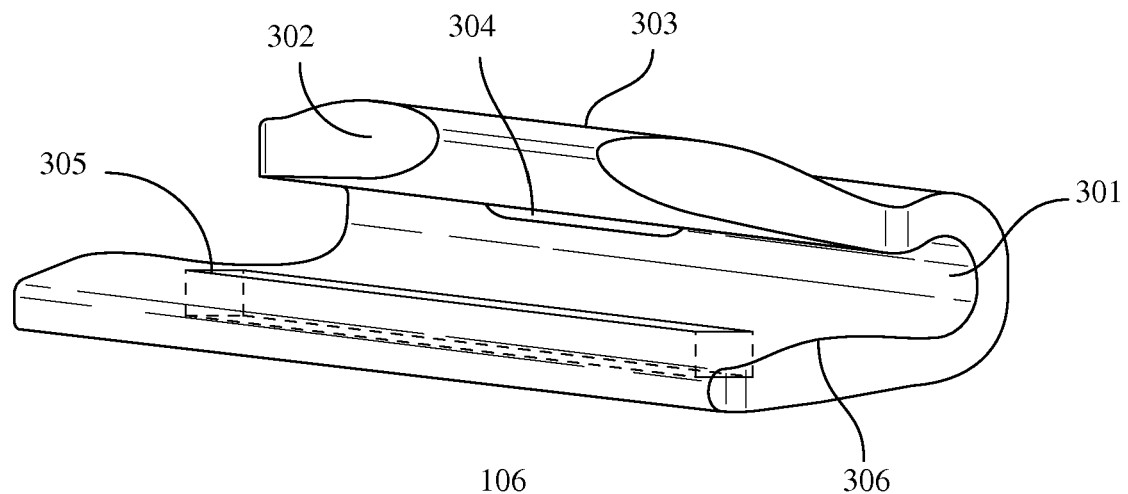
FIG. 3 shows an exemplary receiver of the tourniquet from FIG. 1.

As illustrated in FIG. 3, the receiver 106 includes a hook-shaped catch 301 that the round side bar 401 of the slider 107 (See FIG. 4) can be placed into or removed from by the user on demand through application of the receiver flange 302. A lip portion 303 of the receiver is the narrower portion of the receiver 106 and facilitates ease of placement for the round side bar 401 of the slider 107, and the bar locks the hook slider into place.

With respect to FIG. 3, in some embodiments, the hook-shaped catch 301 (or slider niche) is sized and shaped to mate with and receive the slider 107 and lock the slider 107 securely in place. The receiver flange 302 guides and provides an easy placement for the slider 107 which locks the retaining cover 103 in place. The flange 302 slopes upward to facility placement. The lip 303 is a narrower part of the receiver 106 to provide an easy placement with the receiver flange 302 for the slider 107. A bar 304 hangs down from the lip 303. The bar 304 supports locking of the hook slide and prevents unintentional displacement (dislodging) of the slider 107 from the receiver 106. The bar 304 allows the slider 107 to "snap" or audibly "click" when the slider 107 and receiver 106 are properly mated. A supporter 306 is a thicker portion of the receiver 106 that structurally supports the receiver slot 305. The receiver slot 305 is a space for a receiver holder to connect the receiver 106 to the retaining cover 103 or reservoir chassis 102.

Figure 4:
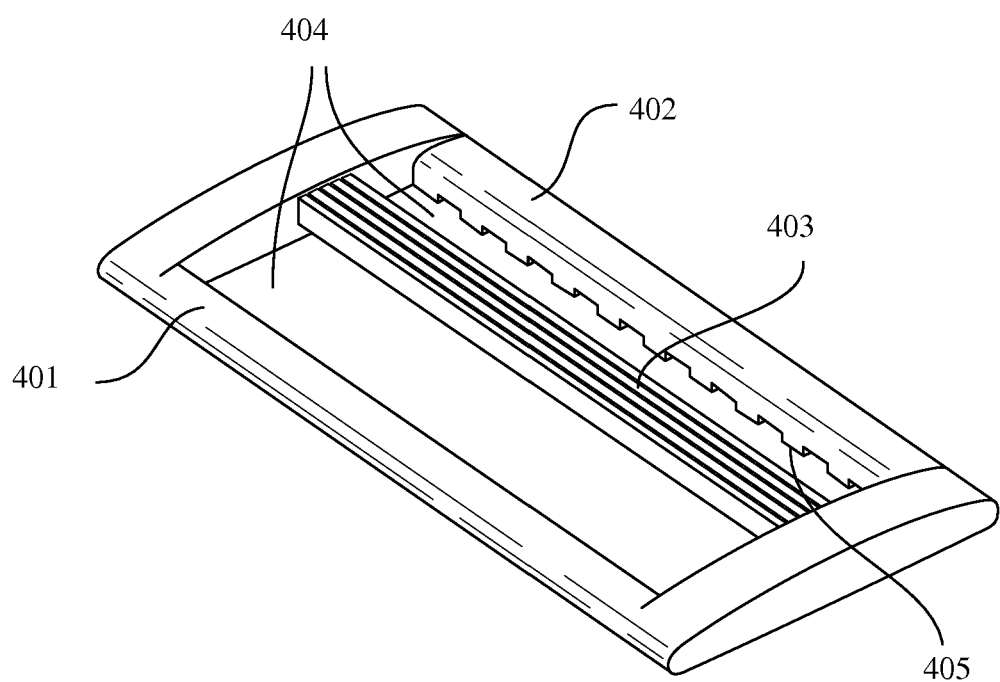
FIG. 4 shows an exemplary slider of the tourniquet from FIG. 1.
Figure 5A:
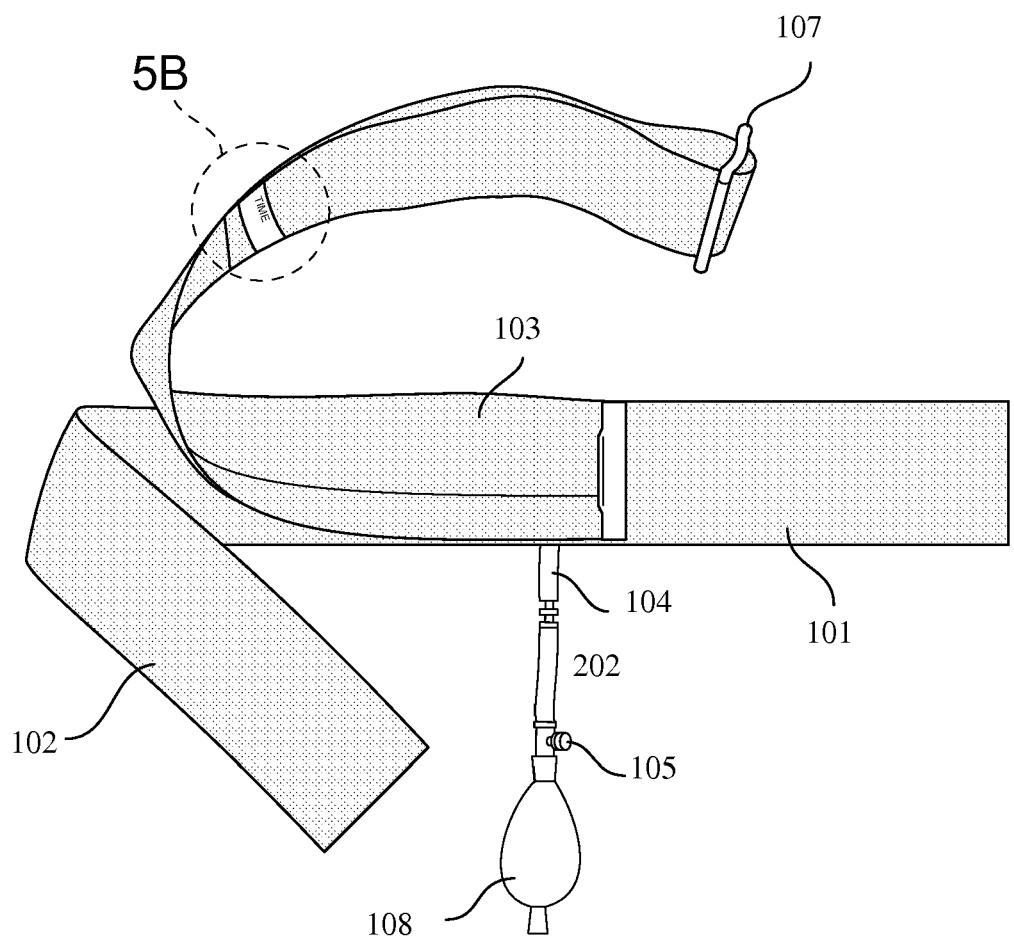
FIG. 5A shows an additional view of a pneumatic tourniquet according to embodiments of the present invention.
Figure 5B:
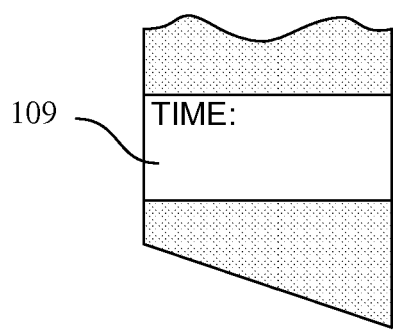
FIG. 5B is a detail view on an enlarged scale of a portion of the tourniquet from FIG. 5A.
Figure 6:
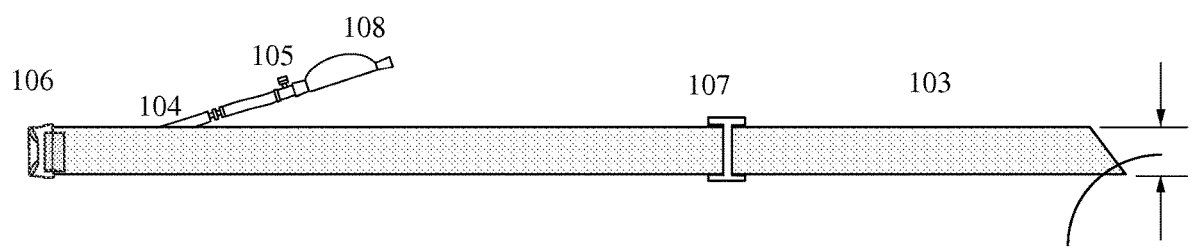
FIG. 6 shows an additional view of a pneumatic tourniquet according to embodiments of the present invention.
Figure 7:
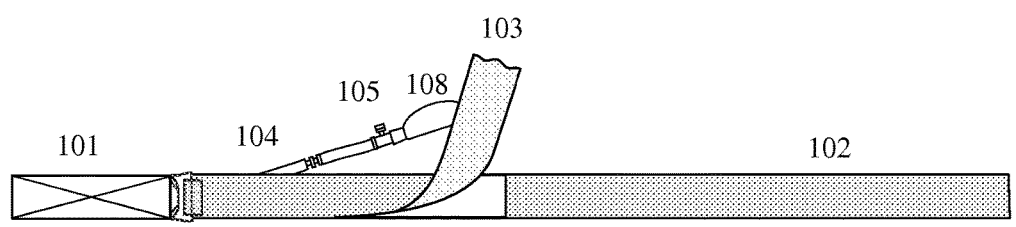
FIG. 7 shows an additional view of a pneumatic tourniquet according to embodiments of the present invention.

With reference to FIG. 4, the slider 107 functions as a friction buckle that is operable to be placed anywhere on the retaining cover 103. The square side bar 402 of the slider 107 with protruding grippers 405 facilitates friction when the round side bar 501 is placed into the receiver 106 (See FIG. 3). As such, the slider 107 reduces slippage, yet allows excess slack to be removed from the diameter of the circumferential tourniquet body upon demand from the user with an upward pulling motion of the retaining cover 103. Furthermore, the retaining cover 103 can be pre-routed through the slider 107, thus avoiding the necessity to route the retaining cover 103 through the slider 107 during use.

Avoiding the need to route the retaining cover 103 through the slider 107 is one of the major advantages of the present inventive concept. Under duress or in emergency situations, many users experience compromised fine motor skills. One example of a prior art tourniquet requires the user to route a strap through two specific slots in a buckle in a specific order. Studies showed that in a large number of failures of the prior art tourniquet resulting in death, the user had routed the strap through the buckle incorrectly. The present inventive concept addresses this known problem by adding a feature that makes it difficult or impossible to pull the terminal end through the buckle. In some embodiments, the terminal end of the retaining cover 103 is folded over on to itself. This creates a "stop" that discourages the user from pulling the retaining cover 103 out of the slider 107. In some embodiments, the folded-over terminal end is sewn such that it cannot be unfolded. In some embodiments, the folded-over terminal end includes an insert, preferably plastic, to increase the size of the "stop" and further decreasing the ability of the user to pull the terminal end through the slider 107.

With respect to FIG. 4, in some embodiments, the slider 107 includes a round edge 401 (or round side bar). The round side bar 401 is sized and shaped to interface with the receiver 106. The round side bar 401 is sized and shaped to allow for articulation when mated with the receiver 106. The slider 107 further includes a frame 402 (or square side bar). The square side bar 402 gives support, structure and shape to the slider 107. In some embodiments, the slider 107 will be a distinctive color to easily and quickly visually distinguish the slider's position relative to the retaining cover 103. For example, in some embodiments, the slider 107 is coyote brown. In some embodiments, the slider 107 includes a slider friction bar 403. The slider friction bar 403 provides friction and inhibits the release of tension when the tourniquet is applied. The friction bar 403 is positioned higher than the side bars 401 and 402. The friction bar 403 is sized and shaped to lock the slider 107 in position when the tourniquet is applied. The slider 107 further includes slider gaps 404. The retaining cover 103 is routed through the slider gaps 404 with dual hook and loop fasteners on the retaining cover 103 side that faces toward the slider friction bar 403. The square side bar 402 of the slider 107 also includes grippers 405. The grippers 405 facilitate friction when the round slider bar 401 is placed into the receiver 106. This stops slippage, yet allows excess slack to be removed from the retaining cover 103 continuous loop upon demand with an upward pulling motion of the retaining cover 103.

Together, the slider 107 (See FIG. 4) and the receiver 106 (See FIG. 3) function as a buckle, so as to create a continuous loop of the tourniquet. Adjustments can be made, via the slider 107, for shortening or lengthening the continuous loop once applied, and/or the slider 107 can be attached or detached from the receiver 106 to facilitate ease of application by the user.

In some embodiments, certain portions of the tourniquet, such as the reservoir chassis 102 and the retaining cover 103 may be made from various types of elastic and/or inelastic flexible material, such as woven fabric, vinyl, leather, neoprene, nylon, etc. Additionally, other components of the tourniquet (e.g., receiver 106 and slider 107) may be made from rigid or semi-rigid materials, such as various types plastics, metals, or the like. Furthermore, portions of the bladder 200, including the bladder 200 itself or the nipple 104, tubing 202, and pump 108, may be made from various materials that are flexible but operable to securely hold fluid therein, such as neoprene, polyurethane, other plastic, or other similar material.

While the present general inventive concept has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

It is also to be understood that the following claims are intended to cover all of the generic and specific features of the invention herein described, and all statements of the scope of the invention which, as a matter of language, might be said to fall therebetween. Hence, the proper scope of the present general inventive concept should be determined only by the broadest interpretation of the appended claims so as to encompass all such modifications as well as all relationships equivalent to those illustrated in the drawings and described in the specification.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed is:

1. A method of making a tourniquet apparatus for restricting blood flow in a limb, the method comprising:
sealing an elongated bladder such that the elongated bladder is moveable between an inflated configuration and a deflated configuration, the inflated and deflated configurations of the elongated bladder being associated with respective constricted and unconstricted configurations of the tourniquet;
inserting the elongated bladder into an elongated reservoir chassis such that a main section of the elongated reservoir chassis envelops the bladder, wherein the tourniquet apparatus is moveable to an engaged configuration by wrapping the elongated reservoir chassis around the limb, thereby creating a first loop;
attaching a proximal end of a retaining cover to a proximal end of the main section of the elongated reservoir chassis, wherein the retaining cover is operable to cover and protect the elongated reservoir chassis when the tourniquet apparatus is in the engaged configuration, thereby forming a second loop;
connecting a receiver to at least one of the elongated reservoir chassis or the retaining cover proximate to the proximal end of the retaining cover; and
connecting a slider to the retaining cover such that the slider can be positioned at any point along the retaining cover, thereby dividing the retaining cover into a first portion extending between the slider and the proximal end of the retaining cover and a second portion extending between the slider and a distal end of the retaining cover, the receiver and slider being sized and shaped such that the slider is temporarily locked in position on the retaining cover as a friction buckle when the slider is locked into the receiver.

2. The method of claim 1, wherein the slider includes a round side bar and a square side bar with a plurality of grippers.

3. The method of claim 1, wherein the second loop is formed by mating the slider and the receiver together.

4. The method of claim 1, wherein the receiver includes a hook-shaped catch into which the slider can be placed or removed, and wherein a lip portion of the receiver is narrower than the receiver and facilitates ease of placement of the slider and locks the hook-shaped catch and slider into place.

5. The method of claim 1, wherein an inner surface of the reservoir chassis is configured to selectively secure to an outer surface of the reservoir chassis, thereby creating the first loop.

6. The method of claim 5, wherein each of the inner and outer surfaces of the reservoir chassis include a plurality of corresponding hook and loop fasteners.

7. The method of claim 5, wherein the retaining cover is configured to create a continuous loop for encircling the limb, the retaining cover being configured to prevent slippage of the connection between the inner and outer surfaces of the reservoir chassis, thereby preventing pressure reduction.

8. The method of claim 1, wherein at least one of the reservoir chassis or the retaining cover includes dual hook and loop fasteners such that said at least one of the reservoir chassis or the retaining cover can be attached to itself.

9. A method of making a tourniquet apparatus, the method comprising:
placing a bladder into a reservoir chassis, the reservoir chassis including a main section that holds the bladder and an extension section connected to and extending from a proximal end of said main section, said extension section being configured to selectively couple to an outer surface of said main section so as to secure the tourniquet apparatus in an engaged configuration, wherein said reservoir chassis forms a first loop when the tourniquet apparatus is in the engaged configuration;

attaching a retaining cover to the reservoir chassis at a position adjacent to where the main section of the reservoir chassis connects to the extension section, said retaining cover being configured to wrap around said reservoir chassis when the tourniquet apparatus is in the engaged configuration, thereby forming a second loop;

attaching a receiver to the retaining cover or the reservoir chassis adjacent to the position where the retaining cover is attached to the reservoir chassis; and attaching a slider to the retaining cover, the slider being sized and shaped to engage with the receiver, the slider being sized and shaped such that the slider can be positioned at any one of a plurality of positions along the retaining cover, wherein wrapping said retaining cover around said reservoir chassis and locking said slider into said receiver when the tourniquet apparatus is in the engaged configuration causes the tourniquet apparatus to move to a secured configuration with the slider temporarily locked in position on the retaining cover.

10. The method of claim 9, wherein the slider includes a round side bar and a square side bar with a plurality of grippers.

11. The method of claim 9, wherein the receiver includes a hook-shaped catch into which the slider can be placed or removed, and wherein a lip portion of the receiver is narrower than the receiver and facilitates ease of placement of the slider and locks the hook-shaped catch and slider into place.

12. The method of claim 9, wherein an inner surface of the reservoir chassis is configured to selectively secure to an outer surface of the reservoir chassis, thereby creating the first loop.

13. The method of claim 12, wherein each of the inner and outer surfaces of the reservoir chassis include a plurality of corresponding hook and loop fasteners.

14. The method of claim 12, wherein the retaining cover is configured to create a continuous loop, the retaining cover being configured to prevent slippage of the connection between the inner and outer surfaces of the reservoir chassis, thereby preventing pressure reduction.

15. The method of claim 9, wherein at least one of the reservoir chassis or the retaining cover includes dual hook and loop fasteners such that said at least one of the reservoir chassis or the retaining cover can be attached to itself.

* * * * *